(12) United States Patent
Kang et al.

(10) Patent No.: US 12,350,230 B2
(45) Date of Patent: Jul. 8, 2025

(54) APPARATUS AND METHOD FOR PROVIDING VIRTUAL REALITY-BASED EYE MOVEMENT EXERCISE AND VISUAL PERCEPTION TRAINING

(71) Applicants: THE ASAN FOUNDATION, Seoul (KR); NUNAPS INC., Seoul (KR); UNIVERSITY OF ULSAN FOUNDATION FOR INDUSTRY COOPERATION, Ulsan (KR)

(72) Inventors: Dong Wha Kang, Seoul (KR); Hyun Taek Lim, Seoul (KR); Byung Joo Lee, Seoul (KR); Rak Kyeun Hong, Guri-si (KR); Yong Hwan Kim, Seoul (KR)

(73) Assignees: THE ASAN FOUNDATION, Seoul (KR); NUNAPS INC., Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 0 days.

(21) Appl. No.: 18/590,552

(22) Filed: Feb. 28, 2024

(65) Prior Publication Data

US 2024/0197554 A1 Jun. 20, 2024

Related U.S. Application Data

(63) Continuation of application No. PCT/KR2022/012772, filed on Aug. 25, 2022.

(30) Foreign Application Priority Data

Sep. 3, 2021 (KR) .......................... 10-2021-0117301

(51) Int. Cl.
*A61H 5/00* (2006.01)
*A61B 3/113* (2006.01)
(Continued)

(52) U.S. Cl.
CPC .............. *A61H 5/005* (2013.01); *A61B 3/113* (2013.01); *G06F 3/013* (2013.01); *G06T 7/0012* (2013.01);
(Continued)

(58) Field of Classification Search
CPC .. A61H 5/00; A61H 5/005; A61H 2201/5023; A61H 2201/5043;
(Continued)

(56) References Cited

U.S. PATENT DOCUMENTS 5,026,151 A 6/1991 Waltuck et al.
10,742,944 B1 * 8/2020 Abou Shousha ...... A61B 3/085
(Continued)

FOREIGN PATENT DOCUMENTS

CN 110812145 A * 2/2020 ............... A61H 5/00
JP H08-206166 A 8/1996
(Continued)

OTHER PUBLICATIONS

English Machine Translation of CN-110812145-A provided by PE2E (Year: 2020).*
(Continued)

*Primary Examiner* — Joseph D. Boecker
*Assistant Examiner* — Brian T Khong
(74) *Attorney, Agent, or Firm* — Studebaker & Brackett PC (57) ABSTRACT

The present invention relates to an apparatus and method for providing virtual reality-based eye movement exercise and visual perception training, wherein a dichoptic presentation is provided in consideration of the deviation of a user's eyeball so as to prevent additional damage to stereoscopic vision due to suppression, and is provided by adjusting the degree of difficulty by changing the locations of visual stimuli on the basis of the level of deviation and training
(Continued)

capability of the user, thus making it possible for the user to not only receive training suitable for the user's condition, but also simultaneously undergo visual perception training including eye exercise (movement) training and stereoscopic perception recognition.

15 Claims, 6 Drawing Sheets

(51) Int. Cl.
    *G06F 3/01*     (2006.01)
    *G06T 7/00*     (2017.01)
    *G06T 7/20*     (2017.01)
    *G06T 7/70*     (2017.01)
    *G06T 19/00*     (2011.01)

(52) U.S. Cl.
    CPC .............. *G06T 7/20* (2013.01); *G06T 7/70* (2017.01); *G06T 19/00* (2013.01); *A61H 2201/0107* (2013.01); *A61H 2201/5007* (2013.01); *A61H 2201/5043* (2013.01); *G06T 2207/30041* (2013.01)

(58) Field of Classification Search
    CPC . A61H 2205/024; A61B 3/113; A61B 3/0041; A61B 3/005; A61B 3/0058; A61B 3/08; A61B 3/085; A61B 3/02; A61B 3/022; A61B 3/032
    See application file for complete search history.

(56) References Cited

U.S. PATENT DOCUMENTS

| | | | | |
|---|---|---|---|---|
| 11,007,109 | B1* | 5/2021 | Hofeldt | A61H 5/005 |
| 11,064,882 | B2 | 7/2021 | Oz et al. | |
| 2016/0270656 | A1* | 9/2016 | Samec | A61B 3/1216 |
| 2020/0329961 | A1* | 10/2020 | Oz | A61H 5/005 |
| 2021/0393123 | A1 | 12/2021 | Oz et al. | |

FOREIGN PATENT DOCUMENTS

| | | |
|---|---|---|
| JP | 2020-509790 A | 4/2020 |
| KR | 10-2018-0034278 A | 4/2018 |
| KR | 10-2018-0083069 A | 7/2018 |
| KR | 10-1937041 B1 | 1/2019 |
| KR | 10-2019-0108903 A | 9/2019 |
| KR | 10-2120112 B1 | 6/2020 |
| KR | 10-2021-0019883 A | 2/2021 |

OTHER PUBLICATIONS

"Request for the Submission of an Opinion" Office Action issued in KR 10-2021-0117301; mailed by the Korean Intellectual Property Office on Mar. 31, 2023.

"Written Decision on Registration" Office Action issued in KR 10-2021-0117301; mailed by the Korean Intellectual Property Office on Jun. 2, 2023.

International Search Report issued in PCT/KR2022/012772; mailed Dec. 6, 2022.

An Office Action; "Notice of Reasons for Refusal," mailed by the Japanese Patent Office on Jul. 30, 2024, which corresponds to Japanese Patent Application No. 2024-514345 and is related to U.S. Appl. No. 18/590,552.

* cited by examiner

APPARATUS AND METHOD FOR PROVIDING VIRTUAL REALITY-BASED EYE MOVEMENT EXERCISE AND VISUAL PERCEPTION TRAINING

CROSS-REFERENCE TO RELATED APPLICATIONS

The present application is a continuation of International Patent Application No. PCT/KR2022/012772, filed on Aug. 25, 2022, which is based upon and claims the benefit of priority to Korean Patent Application No. 10-2021-0117301 filed on Sep. 3, 2021. The disclosures of the above-listed applications are hereby incorporated by reference herein in their entirety.

BACKGROUND

Embodiments of the present disclosure described herein relate to an apparatus and a method for providing virtual reality-based eye movement exercise and visual perception training, and more particularly, relate to an apparatus and a method for providing virtual reality-based movement eye exercise and visual perception training, by which training for improving a visual perception ability, including an eye movement ability and a three-dimensional sense, based on virtual reality may be allowed.

Due to the recent development of media, the incidence of myopia, astigmatism, and strabismus is high. Although there are many studies on disease treatment targeting these patients, research on factors that affect the development of normal vision is still lacking.

Among them, strabismus refers to a condition, in which the two eyes are not aligned properly, and if not treated early, vision may never be restored, and thus, it has to be detected and corrected early in childhood.

If strabismus occurs around the age of 2 to 5, the two eyes of the child see different objects, and accordingly, two completely different images are transmitted to the brain, resulting in visual confusion, by which completely different objects are seen overlapping. In addition, as the patient experiences double vision, in which images appear to be in different places at the same time, the patient ignores images coming from one side to eliminate visual confusion and double vision, and as a result, the patient gives up binocular vision that makes objects appear three-dimensional, and furthermore, the use of the eye that has become strabismus is given up, resulting in amblyopia.

When these symptoms are left untreated, a person will not be able to correct his or her vision even if he or she uses glasses, lenses, or undergoes surgery as an adult, and will end up seeing with only one eye and will be unable to sense a three-dimensional distance. Therefore, when a child has strabismus, it has to be diagnosed quickly and treated appropriately for the sake of vision and the quality of life.

However, when the strabismus angle is small or the fusion power is good, eyeglass treatment or vision correction training may be performed, but the treatment time is long and the cost burden is high.

Accordingly, there is a need to develop a technology that provides and controls eye exercise and visual perception training based on a virtual reality to improve an eye exercise ability and a visual perception ability of a user (test subject), including a three-dimensional sense.

SUMMARY

Embodiments of the present disclosure provide an apparatus and a method for providing virtual reality-based movement eye exercise and visual perception training, by which an additional damage to three-dimensional vision due to restraint by providing dichoptic presentations in consideration of deviation of eyeballs of a user.

Embodiments of the present disclosure also provide an apparatus and a method for providing virtual reality-based eye movement exercise and visual perception training, by which a user may be provided with training that is suitable for his or her state and eye exercise (movement) training and perception of three-dimensional vision are included by adjusting and providing a difficult level through a change of locations of dichoptic presentations based on a deviation level and a training ability of the user to adjust and provide a difficulty level.

The problems that the present disclosure seeks to solve are not limited to the problems mentioned above, and other problems not mentioned may be clearly understood by an ordinary person in the art from the description below.

According to an aspect of the present disclosure, an apparatus for providing virtual reality-based eye movement exercise and visual perception training includes a communication module, an input module, a display module including a plurality of displays including a first display and a second display corresponding to eyes of a test subject, respectively, a memory that stores at least one process that is necessary to provide virtual reality-based eye movement exercise and visual perception training, and a control module that performs a control to perform the virtual reality-based eye movement exercise and visual perception training based on the at least one process, the control module outputs a first image and a second image, which express dichoptic presentations for deriving a binocular disparity on the first display and the second display, acquires visual information on the test subject based on a response of the test subject to the dichoptic presentation received through the input module, and performs a control to change only the dichoptic presentation of, among the first image and the second image, an image output in correspondence to the eye with strabismus, based on the acquired visual information, to perform training, and the visual information includes information on whether strabismus is present in the left eye and the right eye of the test subject, strabismus angle that is information on strabismus degree, and information on a three-dimensional sense.

According to another embodiment of the present disclosure, a method for providing virtual reality-based eye movement exercise and visual perception training, the method being performed by an apparatus includes outputting a first image and a second image including dichoptic presentations for deriving a binocular disparity on a plurality of displays including a first display and a second display provided in the apparatus, wherein the first display and the second display are disposed at positions corresponding to eyes of a test subject, respectively, receiving a response to the test subject to the dichoptic presentations, acquiring visual information on the test subject based on the response, and performing a control to change only the dichoptic presentation of, among the first image and the second image, the image output in correspondence to the eye with strabismus based on the acquired visual information, to perform training, and the visual information includes information on whether strabismus is present in a left eye and a right eye of the test subject, strabismus angle that is information on a strabismus degree, and information on a three-dimensional sense.

Other details of the present disclosure are included in the detailed description and the drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

The advantages and features of the present disclosure, and a method for achieving them will become clear with reference to the embodiments that will be described in detail together with the accompanying drawings. However, the present disclosure is not limited by the embodiments disclosed hereinafter but may be implemented in various different forms, and the embodiments are provided simply to make the disclosure of the present disclosure complete and inform an ordinary person in the art of the scope of the present disclosure, and the disclosure is only defined by the scope of the claims.

The terms used in the specification is for describing the embodiments, and is not intended to limit the present disclosure. A singular expression includes a plural expression unless an exemption is particularly described in the specification. The expression "comprises" and/or "comprising" used in the specification does not exclude presence or addition of one or more other components, in addition to the mentioned components. Throughout the specification, the same reference numerals denote the same components, and the term "and/or" includes one or more combinations of the mentioned components. Although "first", "second", or the like is used to describe various components, it is apparent that the components are not limited by the terns. The terms are used simply to distinguish one component from another component. Accordingly, it is apparent that a first component mentioned hereinafter may be a second component in the technical spirit of the present disclosure.

Unless otherwise defined, all terms (including technical and scientific terms) used herein have the same meaning as commonly understood by those skilled in the art, to which the present disclosure pertains. Furthermore, the terms defined in commonly used dictionaries should not be interpreted in an idealized or overly formal sense unless expressly so defined herein.

The spatially relative terms, such as "below", "beneath", "lower", "above" and "upper", are used to describe an associative relationship between one component and the other components as illustrated in the drawings. The spatially relative terms should be understood as terms including different directions of the components during use or an operation thereof, in addition to the directions illustrated in the drawings. For example, when the components illustrated in the drawings are turned over, a component described as being "below" or "beneath" another component may be positioned "above" the second component. Accordingly, the illustrative term "beneath" or "below" may include all of the upward and downward directions. The component may be oriented in different directions, and thus, the spatially relative terms may be interpreted according to orientations.

As used in the specification, the term "unit" or "module" refers to software or a hardware component, such asFPGA, or ASIC, and the "unit" or "module" module performs certain roles. However, a "part" or "module" is not limited to software or hardware. A "unit" or "module" may be configured to reside on an addressable storage medium and may be configured to run on one or more processors. Thus, as an example, a "part" or "module" refers to components, such as software components, object-oriented software components, class components, and task components, processes, functions, attributes, procedures, subroutines, segments of program code, drivers, firmware, microcodes, circuits, data, databases, data structures, tables, arrays, and variables. The functionality provided within components and "parts" or "modules" may be combined into a smaller number of components and "parts" or "modules" or may be separated into additional components and "parts" or "modules".

Unless otherwise defined, all terms (including technical and scientific terms) used in this specification may be used with meanings that can be commonly understood by those skilled in the art to which the present disclosure pertains. Additionally, the terms defined in commonly used dictionaries are not interpreted ideally or excessively unless clearly specifically defined.

Hereinafter, embodiments of the present disclosure will be described in detail with reference to the attached drawings. A test subject referred to in the following description refers to a user who performs eye exercise and visual perception training by using an apparatus for providing virtual reality-based eye movement exercise and visual perception training according to an embodiment of the present disclosure.

Figure 1:
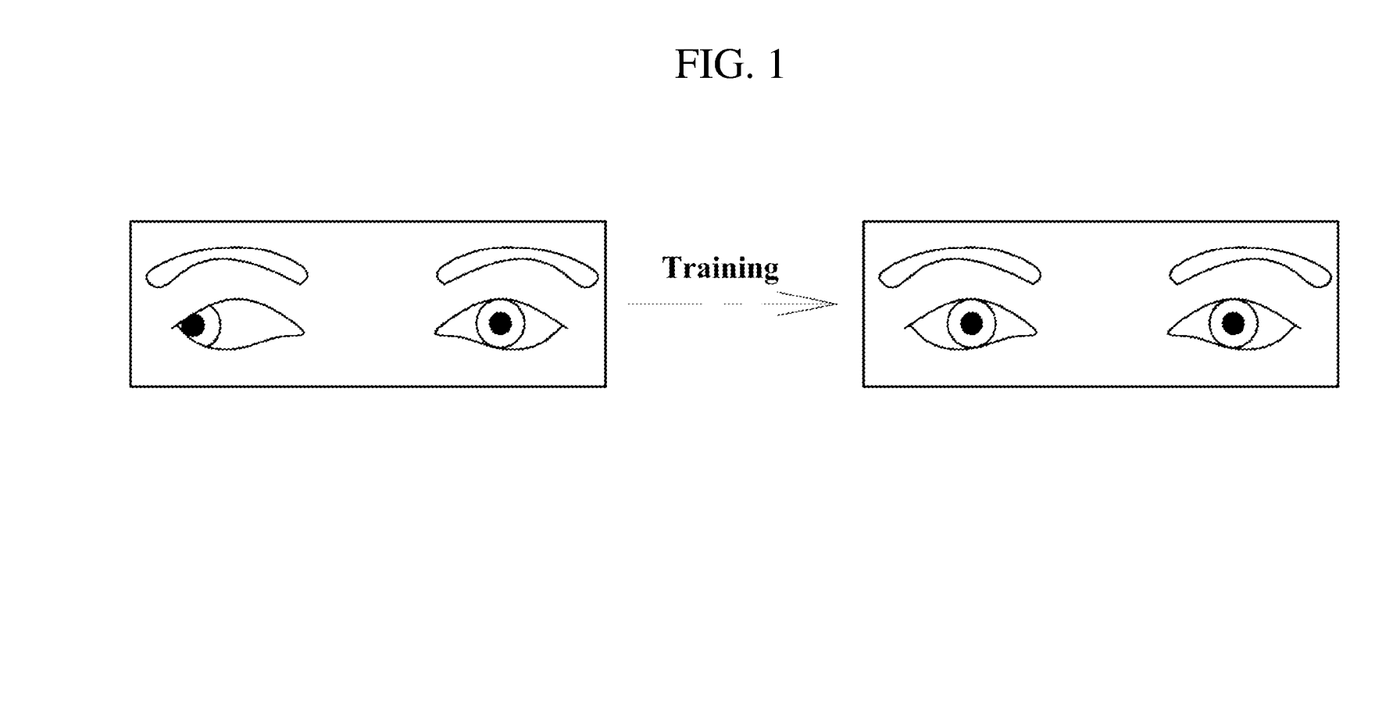
FIG. 1 is a view illustrating the concept of strabismus and training for improving a visual ability and a three-dimensional sense of eyes.

FIG. 1 is a view illustrating the concept of strabismus and training for improving a visual ability and a three-dimensional sense of eyes.

Strabismus is a vision disorder, in which the two eyes are not aligned and look at different points. When one eye looks straight ahead, the other eye turns inward or outward, or upward or downward. The eyes may always be turned, but the eyes that are turned intermittently may look straight ahead at some moments, and the eyes that were looking straight ahead may turn intermittently.

FIG. 1 illustrates an example of a case, in which exotropia exists in the right eye of a test subject, and when the test subject looks straight ahead, the left eye looks straight ahead, but the right eye turns outward.

To improve the visual ability and the three-dimensional ability of the eyes of the test subject, training for bring the right eye inward, that is, to the center, has to be performed repeatedly.

The present disclosure allows these eye exercises and visual perception training to be performed based on virtual reality.

Figure 2:
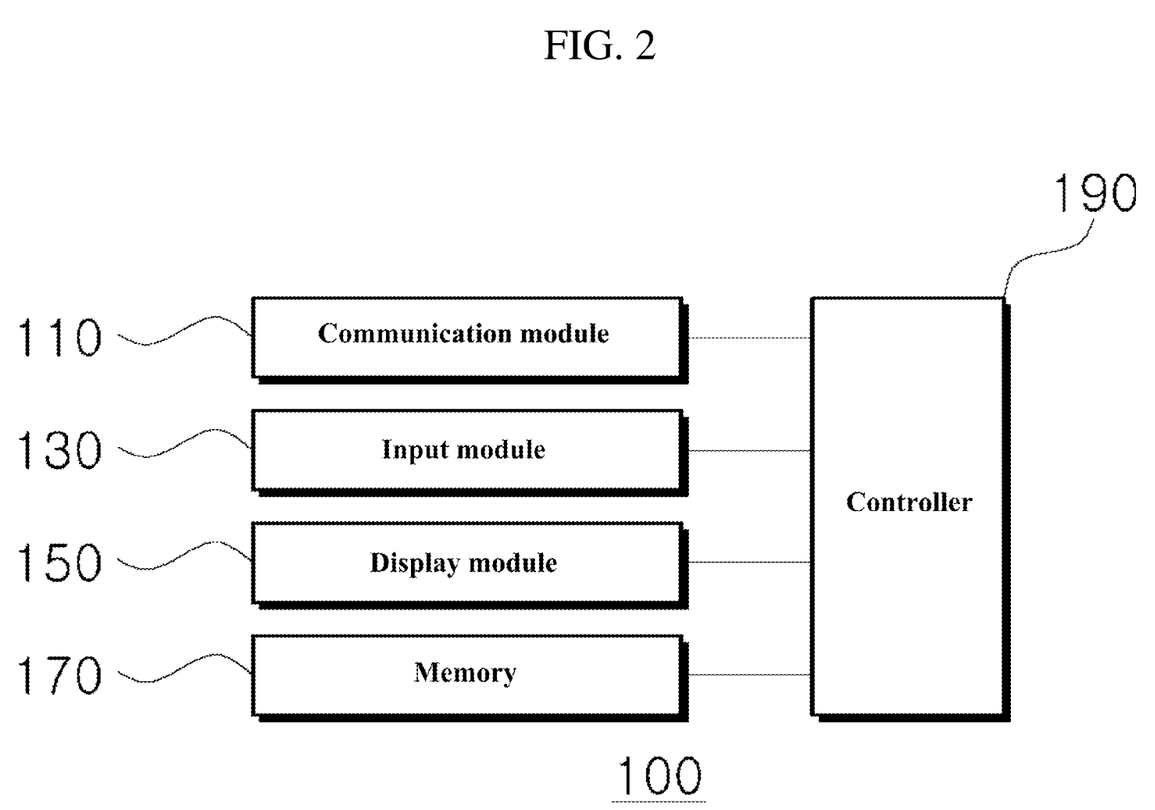
FIG. 2 is a block diagram illustrating a configuration of an apparatus for providing virtual reality-based eye movement exercise and visual perception training according to an embodiment of the present disclosure.

FIG. 2 is a block diagram illustrating a configuration of the apparatus for providing virtual reality-based eye movement exercise and visual perception training according to an embodiment of the present disclosure.

Referring to FIG. 2, the apparatus for providing virtual reality-based eye movement exercise and visual perception training (hereinafter referred to as 'a training providing apparatus') 100 according to an embodiment of the present disclosure includes a communication module 110, an input module 130, a display module 150, a memory 170, and a control module 190.

The communication module 110 performs wired or wireless communication with at least one external device (a server or the like). In particular, when wireless communication is performed, wireless signals are transmitted and received in a communication network based on wireless Internet technologies.

The wireless Internet technologies, for example, include Wireless LAN (WLAN), wireless-fidelity (Wi-Fi)®, Wi-Fi Direct®, digital living network alliance (DLNA), wireless broadband (WiBro), and worldwide interoperability for microwave access (WiMAX)®, high speed downlink packet access (HSDPA), high speed uplink packet access (HSUPA), long term evolution (LTE), and long term evolution-advanced (LTE-A), and the training providing apparatus 100 transmits and receives data according to at least one wireless Internet technology, including the Internet technologies that are not listed above.

For short range communication, short-range communication may be supported using at least one of Bluetooth™, radio frequency identification (RFID), infrared data association (IrDA), ultra wideband (UWB), ZigBee®, near field communication (NFC), wireless-fidelity (Wi-FI)®, Wi-Fi Direct®, and wireless universal serial bus (USB) technologies. Then, the short-range wireless communication network may be a short-range wireless personal area network.

The input module 130 may acquire a signal corresponding to the input of the test subject. For example, the input module 130 may acquire an input from the test subject for measurement or training, a response to a visual stimulus that is provided through the display module 150, and the like.

Then, the input module 130 may include a keyboard, a keypad, a button, a jog shuttle, and a wheel. Furthermore, the input of the test subject in the input module 130, for example, may be a button press, a touch, or a drag.

The input module 130 may include a separate module that is connected to the training providing apparatus 100 wirelessly or by wire. For example, the training providing apparatus 100 may provide an image for measurement or training through the display module 150 that is mounted and attached to the head of the test subject, and may receive a response from the test subject through the input module including a separate module that is given to a hand of the test subject.

The display module 150 outputs a video or an image. For example, the display module 150 may include an LCD, OLED, or AMOLED display.

The display module 150 may include a plurality of first displays and a plurality of second displays corresponding to the eyes (the left eye and the right eye) of the test subject, respectively. Here, the first display may output a first image, and the second display may output a second image. Then, the first image and the second image are provided to express dichoptic presentations for inducing a binocular disparity, and may be any one of the same images, images that at least partially overlap each other, and images that do not overlap each other. Here, the dichoptic presentations are sinusoidal grid dichoptic presentations each having a frame and a specific shape, and include a reference stimulus and a target stimulus.

Here, the display module 150 may include the first display and the second display while they are physically separated from each other, or may be set to be divided into left and right areas of one display.

The memory 170 stores not only at least one data (information) and at least one process that are necessary for providing virtual reality-based eye movement exercise and visual perception training but also various data (information). For example, a program for performing training, at least one test subject information (personal information, visual information, response information, or training results), various reference values that serve as a basis for measuring a strabismus angle and/or a three-dimensional sense, a measured image, or a training imaged may be stored as data. In addition, the memory 170 stores various commands and algorithms for executing a method for providing virtual reality-based eye movement exercise and visual perception training.

Furthermore, the memory 170 may include at least one type of a storage medium of a memory (e.g., an SD or XD memory) of a flash memory type, a hard disk type, a multimedia card micro type, a card type, a random access memory (RAM), a static random access memory (SRAM), read-only memory (ROM), an electrically erasable programmable ROM (EEPROM), a programmable read-only memory (PROM), a magnetic memory, a magnetic disk, and an optical disk. Furthermore, the memory 170 may store information temporarily, permanently, or semi-permanently, and may be provided as an embedded or detachable type.

The control module 190 is provided for controlling components in the training providing apparatus 100 or processing and calculating various information, and performs a control to perform virtual reality-based eye movement exercise and visual perception training based on at least one process stored in the memory 170.

The control module 190 outputs a first image and a second image that express the dichoptic presentations for inducing a binocular disparity on the first display and the second display, respectively, and acquire visual information on the test subject based on the response of the test subject to the dichoptic presentations received through the input module 130. Thereafter, the control module 190 perform control to perform training by changing only the dichoptic presentation of, among the first image and the second image, an image that is output in correspondence to the eye with strabismus based on the acquired visual information. Then, the first image and the second image express the same dichoptic presentation, and cause the image output in correspondence to the eye with strabismus to have a visual deviation depending on the acquired visual information.

In other words, the control module 190 outputs the first image and the second image that express dichoptic presentations to the left and right eyes of the test subject, respectively, and performs a control to perform eye movement training by changing, among the two images, only the image that is output in correspondence to the eye with strabismus while not changing the image that is output in correspondence to the eye that does not have strabismus. In other words, training is performed to focus, among the two eyes of the test subject, the eye that has strabismus in a specific direction.

Meanwhile, the visual information may include at least one of information on the presence or absence of strabismus for the left and right eyes of the test subject, a strabismus angle that is information on a degree of strabismus, and a three-dimensional sense information.

The control module 190 may measure the strabismus angle of the test subject by causing the dichoptic presentations included in the first image and the second image are combined into one image to measure a movement distance of a gaze of the test subject. Furthermore, the control module 190 may receive a response to a stimulus that causes a three-dimensional feeling in the first display and the second display for the dichoptic presentations, and may receive a response to whether a direction of the three-dimensional sense is concave or convex with respect to the stimulus that causes the three-dimensional sense to measure the three-dimensional feeling of the test subject.

The control module 190 may be implemented by software or hardware, or a combination thereof. For example, in hardware, the control module 190 may be implemented by a field programmable gate array (FPGA), an application specific integrated circuit (ASIC), a semiconductor chip, or other various types of electronic circuits. Furthermore, for example, in software, the control module 190 may be implemented by a logic program or various computer languages that are executed according to the above-described hardware.

Unless otherwise mentioned in the following description, an operation of the training providing apparatus 100 may be understood as being performed under the control of the control module 190.

The training providing apparatus 100 according to an embodiment of the present disclosure may include various devices capable of performing computational processing. For example, the training providing apparatus 100 may include a desktop PC, a mobile phone, a smartphone, a laptop computer, a personal digital assistant (PDA), a portable multimedia player (PMP), a slate PC, a tablet PC, an ultrabook, and a wearable device.

Meanwhile, the training providing apparatus 100 may include a head mounted device (HMD) that is mounted on the head of the test subject to display an image, a head mounted device, such as smart glasses or smart goggles, or a display device, such as a mobile phone, which may be held on the head mounted device to be used.

Meanwhile, the training providing apparatus 100 illustrated in FIG. 2 corresponds to an embodiment, and the present disclosure is not limited thereto. For example, when the display module 150 is implemented by a touch screen, the display module 150 may serve as the input module 130. In this case, depending on selection, the separate input module 130 may not be provided, or the input module 130 that performs limited functions, such as a volume control, a power button, and a home button may be provided. Furthermore, the display module 150 may be provided in a form of an image output port that transmits image information to an external display device.

Figure 3:
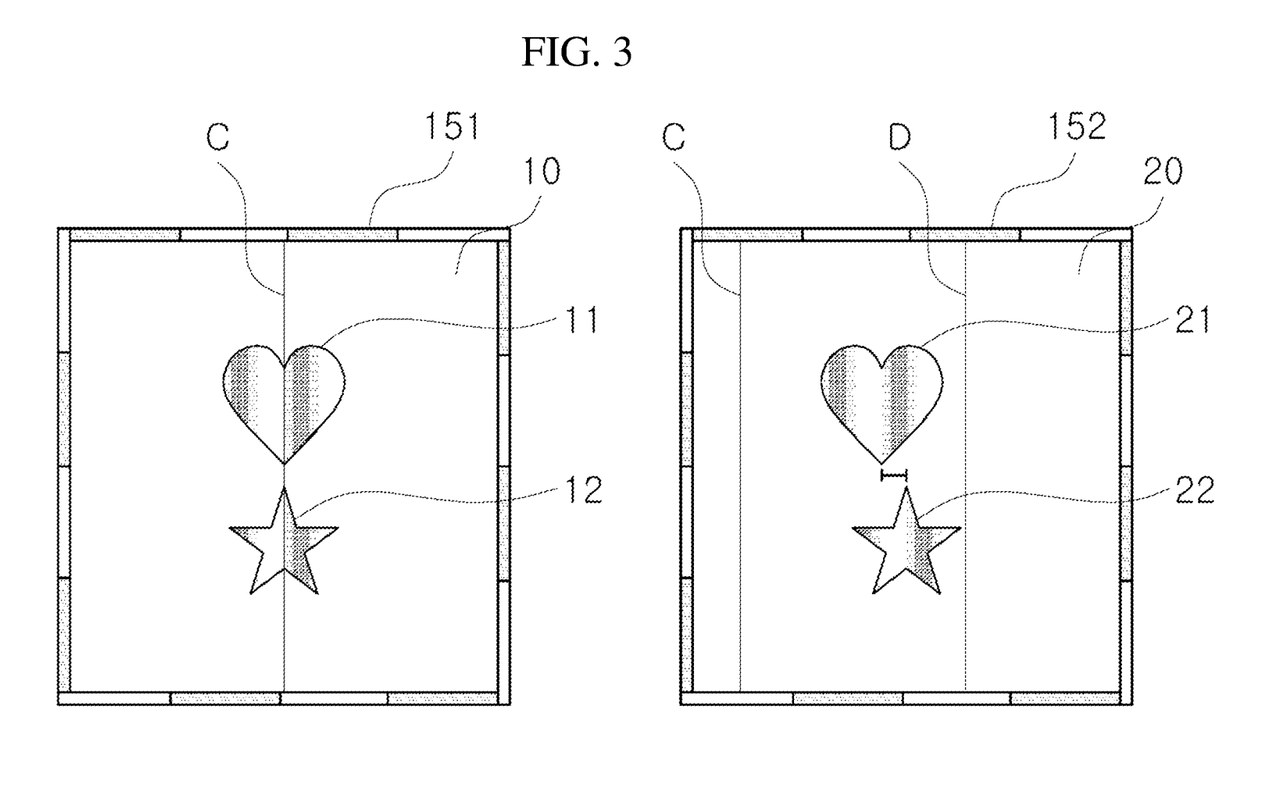
FIG. 3 is a view illustrating an example of an image that is output through a display module of an apparatus for providing virtual reality-based eye movement exercise and visual perception training according to an embodiment of the present disclosure.

FIG. 3 is a view illustrating an example of an image that is output through the display module of the apparatus for providing virtual reality-based eye movement exercise and visual perception training according to an embodiment of the present disclosure, in which a test subject having exotropia in the right eye performs training. Furthermore, FIG. 3 illustrates a display module that is visible when the test subject wears the training providing apparatus 100, including a first display 151 that is disposed in an area corresponding to the left eye of the test subject and a second display 152 disposed in an area corresponding to the right eye of the test subject.

As described above, the dichoptic presentation includes a reference stimulus and a target stimulus, and the dichoptic presentation included in, among the first image and the second image, the image that is output in correspondence to the eye with strabismus is disposed at a position that is determined based on the strabismus angle in the corresponding image, and is provided such that there is a difference between the central axis of the reference stimulus and the central axis of the target stimulus in the image. Meanwhile, the dichoptic presentation included in, among the first image and the second image, the image that is output in correspondence to the eye without strabismus is disposed with respect to a center of the image, and the central axis of the reference stimulus and the central axis of the target stimulus in the image are provided to be disposed on the same line.

Referring to FIG. 3, a first image 10 is output through the first display 151 corresponding to the eye without strabismus, and a second image 20 is output through the second display 152 corresponding to the eye with strabismus.

Then, both of the first image 10 and the second image 20 express dichoptic presentations, and include a heart-shaped object as a reference stimulus and a star-shaped object as a target stimulus. However, a dichoptic presentation is disposed at a center of the first image 10 corresponding to the left eye without strabismus, but a dichoptic presentation is disposed in the second image 20 corresponding to the right eye with strabismus at a position that is reflected based on the strabismus angle of the test subject. Furthermore, a central axis "C" of a first reference stimulus 11 expressed in the first image 10 (matched with the central axis of the first image 10) and a central axis "D" of a first target stimulus 12 are disposed on the same line, whereas the central axis "C" of a second reference stimulus 21 expressed in the second image 20 and the central axis "D" of a second target stimulus 22 are disposed to have a difference.

Meanwhile, when the training providing apparatus 100 provides eye exercise and visual perception training of the test subject, it moves the central axis "D" of the second target stimulus 22 toward the central axis "C" of the second reference stimulus 21 by a preset distance over a preset time period to cause the test subject to perform training. Here, the preset distance and the preset time period may be set based on visual information for the test subject, and may be set to be changed depending on a training ability or needs of the test subject.

Figure 4:
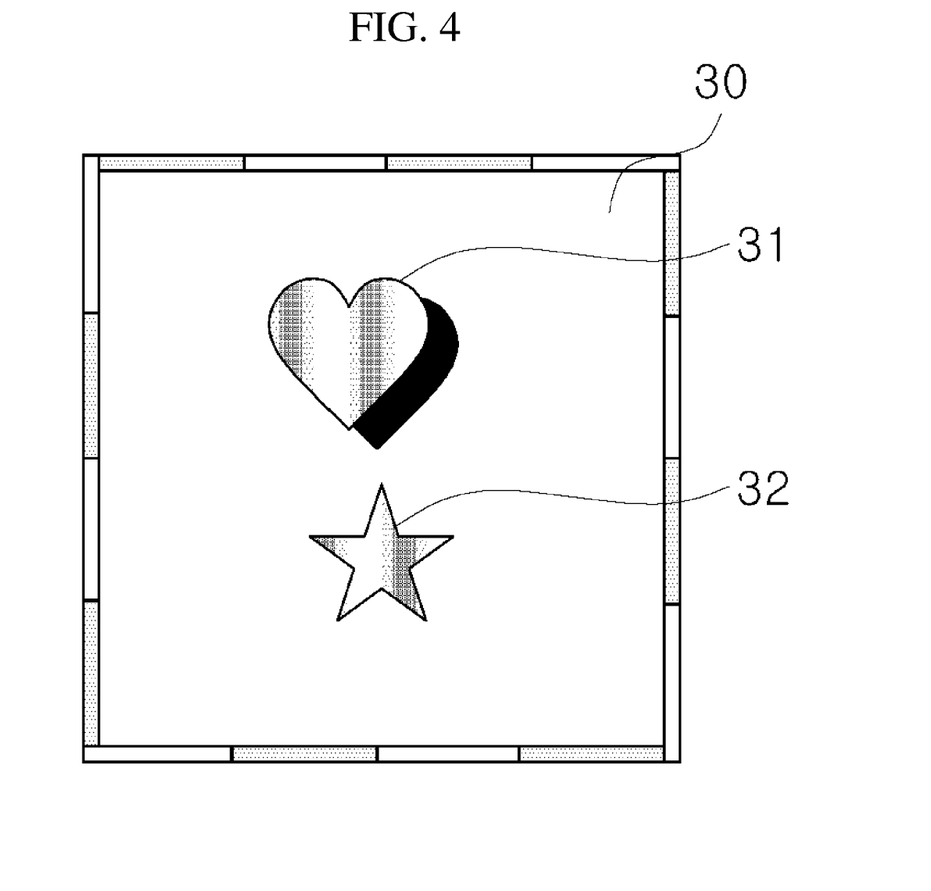
FIG. 4 illustrates an example of a third image which is induced by an apparatus for providing virtual reality-based eye movement exercise and visual perception training according to an embodiment of the present disclosure, and in which visual stimuli of a first image and a second image are combined.

FIG. 4 illustrates an example of a third image which is induced by an apparatus for providing virtual reality-based eye movement exercise and visual perception training according to an embodiment of the present disclosure, and in which visual stimuli of a first image and a second image are combined.

As illustrated in FIG. 3, the first image 10 and the second image 20 of the test subject are provided simultaneously through the first display 151 and the second display 152, respectively such that the two dichoptic presentations are induced to be combined into one image, and through this, the test subject may identify the dichoptic presentation as in the third image 30. Accordingly, the test subject cannot feel the three-dimensional sense through a third target stimulus 32, but may feel the three-dimensional sense through a third reference stimulus 31.

Figure 5:
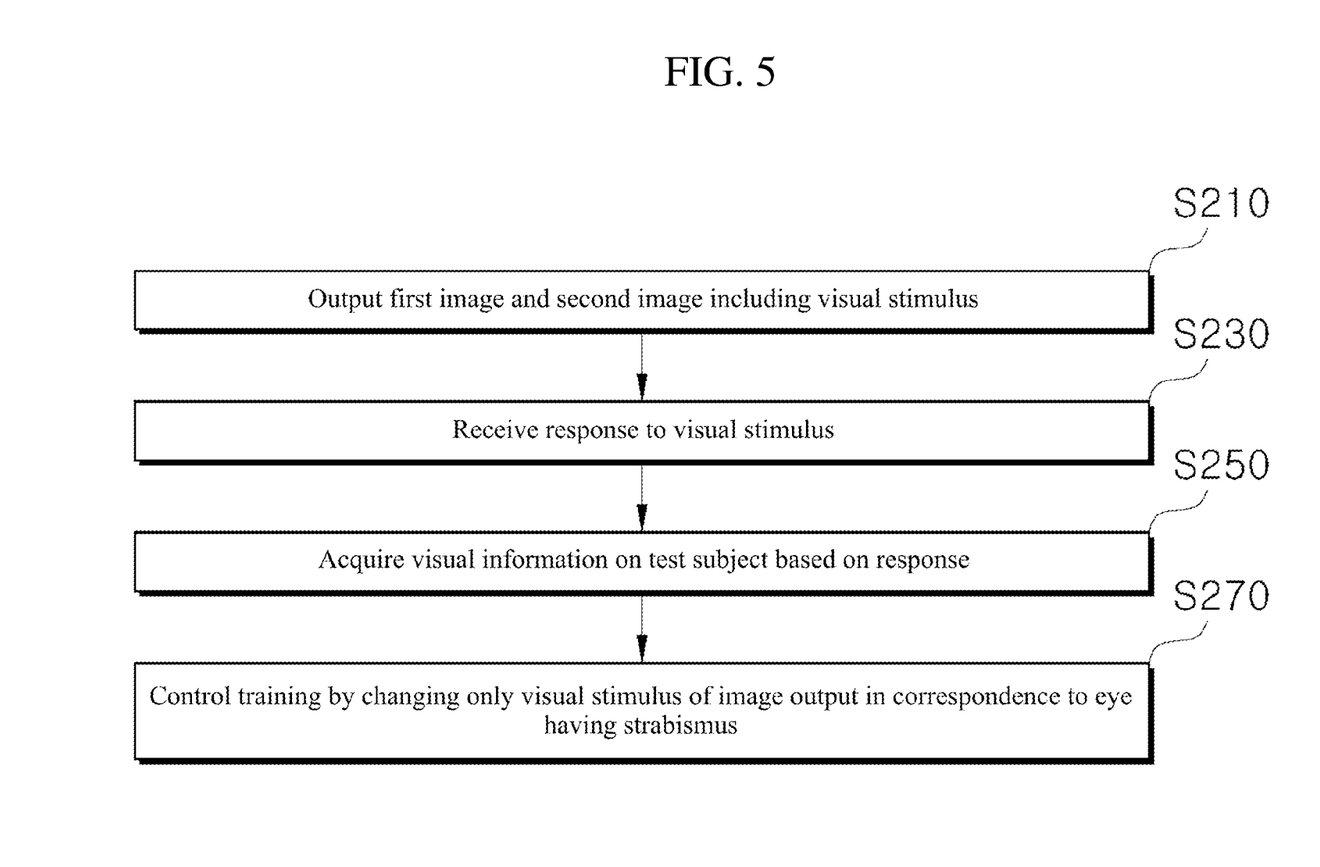
FIG. 5 is a flowchart illustrating a method for providing virtual reality-based eye movement exercise and visual perception training according to an embodiment of the present disclosure.

FIG. 5 is a flowchart illustrating a method for providing virtual reality-based eye movement exercise and visual perception training according to an embodiment of the present disclosure.

The first image and the second image including dichoptic presentations for inducing a binocular disparity on the plurality of displays including the first display and the second display provided in the training providing apparatus 100 are output and provided to the test subject (S210), and a response to the dichoptic presentations is received from the test subject (S230).

Based on the response, visual information on the test subject is acquired (S250), and based on the acquired visual information, only the dichoptic presentation of, among the first image and the second image, the image that is output in correspondence to the eye with strabismus is changed to control the training provided to the test subject (S270).

In detail, when the training is controlled, the test subject controls the training of the corresponding eye while the central axis of, among the reference stimulus and the target stimulus included in the image output in correspondence to the eye with strabismus, the target stimulus is moved toward the reference stimulus.

Figure 6:
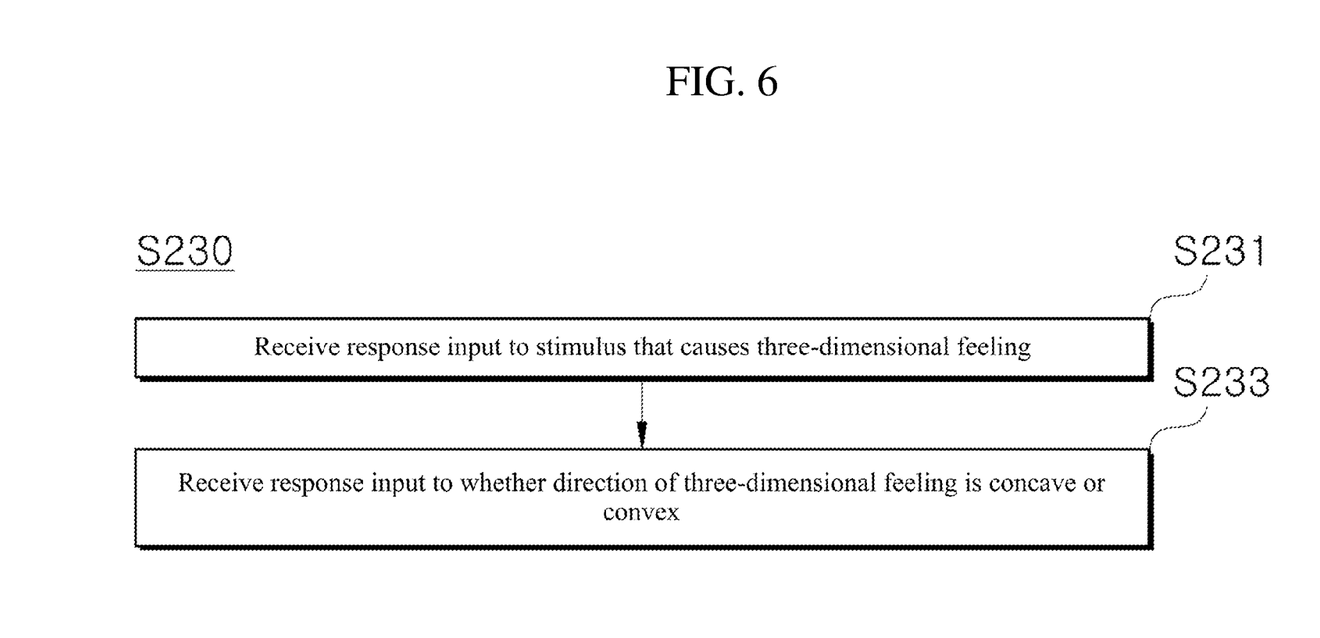
FIG. 6 is a flowchart illustrating a process of measuring a three-dimensional sense in visual information on a test subject to provide virtual reality-based eye movement exercise and visual perception training according to an embodiment of the present disclosure.

FIG. 6 is a flowchart illustrating a process of measuring a three-dimensional sense in visual information on a test subject to provide virtual reality-based eye movement exercise and visual perception training according to an embodiment of the present disclosure.

Through, among the operations of FIG. 5 described above, an operation of acquiring visual information, the training providing apparatus 100 may acquire a strabismus angle and a three-dimensional sense information as visual information of the test subject. Among them, the three-dimensional sense information may be acquired through a response of the test subject.

In detail, a response to a stimulus that causes the three-dimensional sense in the first display and the second display for the dichoptic presentation is received (S251), and a response to whether a direction of the three-dimensional sense is concave or convex with respect to the stimulus that causes the three-dimensional sense is received (S253). Accordingly, the training providing apparatus 100 may measure the three-dimensional sense of the test subject.

Meanwhile, the operations of the method or algorithm described in relation to the embodiment of the present disclosure may be implemented directly in hardware, implemented as a software module executed by hardware, or a combination thereof. The software module may reside in a random access memory (RAM), a read only memory (ROM), an erasable programmable ROM (EPROM), an electrically erasable programmable ROM (EEPROM), a flash memory, a hard disk, a removable disk, a CD-ROM, or any type of computer-readable recording medium well known in the art, to which the present disclosure pertains.

According to the present disclosure, an additional damage to three-dimensional vision due to restraint may be prevented by providing dichoptic presentations in consideration of deviation of eyeballs of a user.

According to the present disclosure, a user may be provided with training that is suitable for his or her state and eye exercise (movement) training and perception of three-dimensional vision are included by changing locations of dichoptic presentations based on a deviation level and a training ability of the user to adjust and provide a difficulty level.

The effects of the present disclosure are not limited to the effects mentioned above, and other effects not mentioned may be clearly understood by an ordinary person in the art from the description below.

Until now, the embodiments of the present disclosure have been described with reference to the accompanying drawings, but it may be understood that an ordinary person in the art, to which the present disclosure pertains, may carry out the present disclosure in another specific form while not changing the technical spirit or the essential features. Therefore, it should be understood that the embodiments described above are all illustrative, and not restrictive.

What is claimed is:

1. An apparatus for providing virtual reality-based eye movement exercise and visual perception training, the apparatus comprising:
 a head mounted device (HMD) comprising a first display and a second display, wherein the HMD is configured to be mounted on a head of a test subject, and the first display and the second display are configured to be positioned in front of a left eye and a right eye of the test subject, respectively;
 a memory configured to store at least one process that is necessary to provide the virtual reality-based eye movement exercise and visual perception training; and
 a processor configured to the virtual reality-based eye movement exercise and visual perception training based on the at least one process,
 wherein the processor is configured to:
 display a first image and a second image, which express a dichoptic presentation for deriving a binocular disparity, on the first display and the second display;
 receive, from the test subject, a response to the dichoptic presentation;
 acquire visual information on the test subject based on the received response; and
 perform a first control to change only the dichoptic presentation of, among the first image and the second image, an image output in correspondence to the left eye or the right eye, which has strabismus, based on the acquired visual information, to perform the virtual reality-based eye movement exercise, and
 wherein the visual information includes information on whether the strabismus is present in the left eye or the right eye of the test subject, a strabismus angle that is information on a strabismus degree, and information on a three-dimensional sense,
 wherein the processor is further is configured to perform a second control to the first display and the second display to provide a stimulus that causes the three-dimensional sense from the dichoptic presentation, receive a response indicating whether a direction of the three-dimensional sense is concave or convex, and measure the three-dimensional sense of the test subject based on the received response, to perform the visual perception training of the three-dimensional sense, and
 wherein the processor simultaneously performs the first control and the second control, such that the virtual reality-based eye movement exercise and the visual perception training of the three-dimensional sense are simultaneously performed.

2. The apparatus of claim 1, wherein the dichoptic presentation comprises sinusoidal grid dichoptic presentations each having a frame and a shape, and the sinusoidal grid dichoptic presentations include a reference stimulus and a target stimulus.

3. The apparatus of claim 2, wherein the dichoptic presentation included in, among the first image and the second image, the image output in correspondence to the left eye or the right eye having the strabismus is disposed at a position determined based on the strabismus angle in the corresponding image, and a central axis of the reference stimulus and a central axis of the target stimulus are disposed to be different.

4. The apparatus of claim 3, wherein the dichoptic presentation included in, among the first image and the second image, the image output in correspondence to the left eye or the right eye not with the strabismus is disposed with respect to a center of the corresponding image, and the central axis of the reference stimulus and the central axis of the target stimulus are disposed on a same line.

5. The apparatus of claim 3, wherein the processor is further is configured to:
gradually move the central axis of the target stimulus over a preset time period by a preset distance toward the central axis of the reference stimulus when the training is controlled to be performed.

6. The apparatus of claim 5, wherein the preset distance and the preset time period are set based on the visual information of the test subject.

7. The apparatus of claim 1, wherein the processor is further configured to:
measure the strabismus angle of the test subject by measuring a movement distance of a gaze while the dichoptic presentation included in the first image and the second image, respectively, is coupled into one image.

8. A method for providing virtual reality-based eye movement exercise and visual perception training, the method being performed by an apparatus comprising a head mounted device (HMD) configured to be mounted on a head of a test subject and having a first display and a second display, which are configured to be positioned in front of a left eye and a right eye of a target subject, respectively, the method comprising:
displaying, on the first display and the second display, a first image and a second image, which express a dichoptic presentation for deriving a binocular disparity;
receiving, from the test subject, a response to the dichoptic presentation;
acquiring visual information on the test subject based on the received response;
performing a first control to change only the dichoptic presentation of, among the first image and the second image, an image output in correspondence to the left eye or the right eye, which has strabismus based on the acquired visual information, to perform the virtual reality-based eye movement exercise;
wherein the visual information includes information on whether the strabismus is present in the left eye or the right eye of the test subject, a strabismus angle that is information on a strabismus degree, and information on a three-dimensional sense; and
performing a second control to the first display and the second display to provide a stimulus that causes the three-dimensional sense from the dichoptic presentation, receiving a response indicating whether a direction of the three-dimensional sense is concave or convex, and measuring the three-dimensional sense of the test subject based on the received response, to perform the visual perception training of the three-dimensional sense,
wherein the first control and the second control are simultaneously performed, such that the virtual reality-based eye movement exercise and the visual perception training of the three-dimensional sense are simultaneously performed.

9. The method of claim 8, wherein the dichoptic presentation comprises sinusoidal grid dichoptic presentations each having a frame and a shape, and the sinusoidal grid dichoptic presentations include a reference stimulus and a target stimulus.

10. The method of claim 9, wherein the dichoptic presentation included in, among the first image and the second image, the image output in correspondence to the left eye or the right eye having the strabismus is disposed at a position determined based on the strabismus angle in the corresponding image, and a central axis of the reference stimulus and a central axis of the target stimulus are disposed to be different.

11. The method of claim 10, wherein the dichoptic presentation included in, among the first image and the second image, the image output in correspondence to the left eye or the right eye not with the strabismus is disposed with respect to a center of the corresponding image, and the central axis of the reference stimulus and the central axis of the target stimulus are disposed on a same line.

12. The method of claim 10, wherein the performing the first control comprises:
gradually moving the central axis of the target stimulus over a preset time period by a preset distance toward the central axis of the reference stimulus.

13. The method of claim 12, wherein the preset distance and the preset time period are set based on the visual information of the test subject.

14. The method of claim 8, wherein the acquiring of the visual information comprises:
measuring the strabismus angle of the test subject by measuring a movement distance of a gaze while the dichoptic presentation included in the first image and the second image, respectively, is coupled into one image.

15. A nonvolatile computer readable recording medium, coupled to a computer and in which a computer program for operating the computer to perform the method for providing virtual reality-based eye movement exercise and visual perception training according to claim 8.

* * * * *